United States Patent [19]

Massart

[11] Patent Number: 5,552,997
[45] Date of Patent: Sep. 3, 1996

[54] METHOD OF CALIBRATING AN ANALYTICAL INSTRUMENT

[75] Inventor: Desire J. L. Massart, Gent, Belgium

[73] Assignee: U.S. Philips Corporation, New York, N.Y.

[21] Appl. No.: 275,099

[22] Filed: Jul. 14, 1994

Related U.S. Application Data

[63] Continuation of Ser. No. 976,624, Nov. 16, 1992, abandoned, which is a continuation of Ser. No. 685,266, Apr. 12, 1991, Pat. No. 5,210,778.

[30] Foreign Application Priority Data

Apr. 20, 1990 [GB] United Kingdom ............. 90 08 922.8

[51] Int. Cl.⁶ ...................................... G12B 13/00
[52] U.S. Cl. ................. 364/571.01; 250/390.07; 364/496
[58] Field of Search ................... 364/496, 498, 364/571.01; 250/390.07, 393, 339.07, 339.09, 339.12, 341.5, 496

*Primary Examiner*—Ellis B. Ramirez
*Assistant Examiner*—Thomas Peeso
*Attorney, Agent, or Firm*—Paul Miller

[57] ABSTRACT

A method of calibrating an analytical instrument, for example an atomic absorption spectrophotometer, comprises measuring the absorbance of a plurality of standards of known concentration (100) and plotting the measured absorbance against concentration (101). A straight line is fitted to the plotted points (102) and a quality co-efficient calculated (103). If the quality co-efficient is acceptable (104) the calibration line is used for measurement of samples (105). If not, then the slope of the line joining each point to the origin is determined and if the slopes are random (107) then a robust regression technique is used to fit the calibration line (108). If outliers are then detected (109) it is determined which points are outliers (110) and appropriate action taken, for example to restrict the range if the last point(s) is/are outliers (111). If the slopes determined in step (106) are not random, then, provided more than 4 points remain (113), the slope of each point with respect to the first point is determined (114). If they are again not random (115), then a curved calibration line is diagnosed, while if they are random, a straight line not passing through the origin is diagnosed (117). In atomic absorption spectroscopy, a straight line not passing through the origin indicates a problem with the blank solution, for example, a problem of contamination.

8 Claims, 4 Drawing Sheets

METHOD OF CALIBRATING AN ANALYTICAL INSTRUMENT

This is a continuation of application Ser. No. 07/976,624, filed Nov. 16, 1992 now abandoned which is a continuation of application Ser. No. 07/685,266 filed Apr. 12, 1991 now U.S. Pat. No. 5,210,778.

The invention relates to a method of calibrating an analytical instrument which uses a comparative technique for determining a constituent of a sample, the method comprising the steps of a) measuring a characteristic of a plurality of standards having different nominal values, b) storing the measured characteristic in association with its corresponding nominal value, c) determining using statistical techniques a best straight calibration line using the stored values, and d) determining the quality of the calibration line.

BACKGROUND OF THE INVENTION

In many chemical analyses a comparative technique is used to determine properties of a sample. This involves the measurement of one or more characteristics of a plurality of standards to produce a calibration curve. For example in atomic absorption spectroscopy a series of standards containing a known range of concentrations of a given element are measured to determine their absorption and a graph of absorption against concentration is plotted. The absorption of an unknown sample is then measured and the concentration of the element to be detected is then determined using the calibration curve. It is generally assumed that at least at lower concentrations the calibration curve will be linear and will pass through the origin. Various techniques can be used for constructing the best straight line calibration curve from the measured absorbance values of the standard solutions, for example as disclosed in a paper entitled "Exploratory Study on Median-based. Robust Regression Methods for Linear Calibration in Atomic Absorption Spectrometric Analysis" by Yuzhu Hu, Jobanna Smeyers-Verbeke and D ésiré L Massart published in Journal of Analytical Atomic Spectroscopy, October 1989, Vol. 4, pages 605–611. In addition, it is known to use statistical techniques to assess the quality of the calibration line as this will indicate the most appropriate statistical technique for to constructing it and such a criterion is defined by Knecht and Stork in Fresenius Z. Anal. Chem, 1974, 270, 97.

While these techniques will enable a straight line to be fitted to the measured points and the quality of that line to be assessed they do not provide an easy analysis of the cause of any lack of quality, that is whether it is due to measurement inaccuracies or to trying to fit a straight line to data which in fact defines a curved calibration line.

SUMMARY OF THE INVENTION

It is an object of the invention to enable the determination of possible causes of lack of quality of a calibration line.

The invention provides a method of calibrating an analytical instrument as set forth in the opening paragraph, characterised by the performance of the further steps, when the quality of the calibration line is not acceptable, of e) determining the slope of the line joining each of the stored measured characteristics and nominal values to the origin, and f) determining whether the slopes have a given order.

By measuring the slopes and finding whether or not they are random it can be determined whether the problem is in the precision of measurement of the standards or the quality of the standards, which will be the case if the slopes are random, or whether the points do not represent a straight line through the origin.

When the slopes are ordered there are two possible explanations. Either the points represent a straight line which does not pass through the origin or they represent a curved line.

Accordingly the method may comprise the further steps when the slopes are in the given order, of g) determining the slope of each stored measured and nominal value with respect to the first stored measured characteristic and nominal value, h) determining whether the slopes have a given order, and if so, i) indicating curvature of the calibration line, or if not, j) indicating that the calibration line does not pass through the origin.

The number of calibration standards used may be between four and six inclusive. With fewer than four measured points the statistical basis of the invention becomes less valid and as the number of standards increase the computational effort involved increases. There is no absolute upper limit apart from that set by the computational speed and the time allowed for computation of the results. At present it is considered that, particularly for atomic absorption spectroscopy, an upper limit of six standards gives an acceptable calibration without requiring unreasonable computation effort. That is, it can be carried out on an IBM PC compatible computer in an acceptable time.

The statistical technique in step c) may be the least squares method. It is generally not desired to use a robust regression method to obtain the calibration function but the robust methods are generally employed in the diagnosis of the reasons for lack of quality and for the elimination of outliers.

The analytical instrument may be an atomic absorption spectrophotometer, the measured characteristic being the absorbance of the standard and the nominal value the concentration of the standard. In which case if an outlier is detected at the maximum standard concentration then curvature of the calibration line at higher concentrations may be indicated and if the absorbance at zero concentration is detected as an outlier then a blank problem may be indicated.

If a statistical technique such as least median of squares method is used it is possible to detect outliers and their position and hence this forms an alternative method of detecting a blank problem which is particularly useful when only four standards are used and also enables detection of curvature at high concentration levels.

The analytical instrument may be an X-ray spectrometer, the measured characteristic being the intensity of the X-rays received by a detector from the standard, and the nominal value being the concentration of the standard.

The invention further provides an atomic absorption spectrophotometer comprising means for storing measured absorbance values of a plurality of standards in association with the concentration values of corresponding standards, means for determining, using statistical techniques, a best straight calibration line, means for determining the quality of the calibration line, means for determining the ratio of absorbance to concentration for each of the measured standards and means for determining whether the ratios have a given order, whereby it can be determined whether a calibration line which is not of acceptable quality is caused by lack of measurement precision.

The atomic absorption spectrophotometer may further comprise means for determining whether the slope of each of the measured standards with respect to the first measured standard are in a given order whereby it can be determined whether a blank problem exists.

The number of standards may lie between four and six inclusive. This gives sufficient statistical validity without requiring unreasonable computing power. The statistical technique may be the least squares method. If an outlier or outliers is/are detected at the highest concentration standard or standards, curvature of the calibration line at high concentrations maybe indicated and the atomic absorption spectrophotometer may comprise means for indicating the region of a linear calibration curve. The atomic absorption spectrophotometer may further comprise means for indicating a blank problem if zero concentration, zero absorbance is detected as an outlier. This provides an alternative method of detecting a blank problem which may be used, for example when only four standards are measured and consequently there are insufficient slopes with respect to the first standard point to give proper statistical validity to the determination of whether the line is straight or curved by noting the order of the slopes.

The atomic absorption spectrophotometer may comprise means for storing measured absorption values of a plurality of standards added to the sample, means for determining, using statistical techniques, a best straight standards addition line, means for determining whether the slopes of each measured sample plus standard point with respect to the sample point is in a given order whereby it can be determined whether curvature of the standard addition line occurs.

The atomic absorption spectrophotometer may further comprise means for determining the quality of the standards addition line and for comparing its slope with that of the calibration line if both are satisfactory to determine whether matrix interference problems exist.

Thus the same method can be applied to the standards addition line as those applied to the calibration line except that the detection of a blank problem is not relevant in that there will always be a sample absorbance and consequently it can only be determined whether a random variation of slopes with respect to the sample absorption occurs.

BRIEF DESCRIPTION OF THE DRAWINGS

The above and other features and advantages of the invention will become apparent from the following detailed description of an exemplary embodiment of the invention with reference to the accompanying drawings, in which.

DESCRIPTION OF THE PREFERRED EMBODIMENTS

Figure 1:
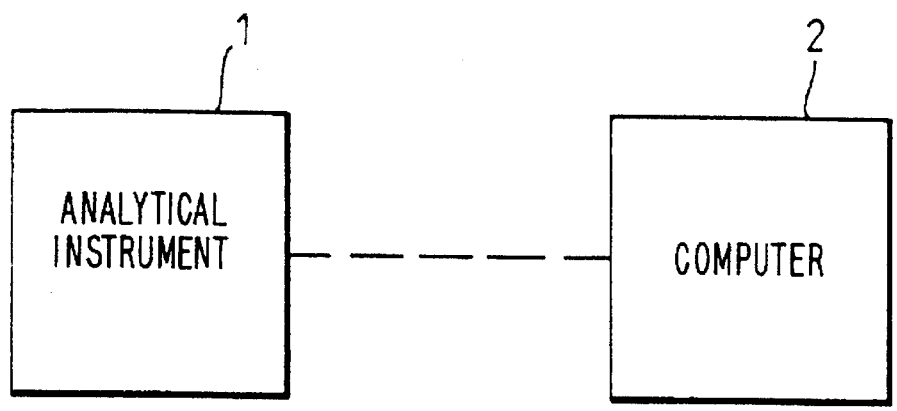
FIG. 1 shows an atomic absorption spectrophotometer according to the invention.

FIG. 1 shows an atomic absorption spectrophotometer according to the invention which comprises a commercial atomic absorption spectrophotometer 1, which may be any convenient instrument, for example that sold by Philips Scientific under the type reference PU9400X. The atomic absorption spectrophotometer is connected to a computer 2 which may be an IBM PC compatible computer available from many manufacturers and which will include an input device such as a keyboard and a video display unit (VDU) for numerical or graphical display of measurements and/or instrument parameters. The computer 2 is arranged to receive the analytical results from the spectrophotometer 1 either by direct connection or by entry of the results read from the spectrophotometer by an analyst and entered into the computer 2 via its keyboard.

The computer 2 may contain software for enabling the analysis of results and storage means for storing the results either temporarily in RAM or semi-permanently on floppy or hard discs. Further, a printer may be provided to enable hard copies of the results to be obtained. The computer 2 also contains software for carrying out parts of the method illustrated in the flow diagram shown in FIG. 2.

As is well known the analysis of samples by atomic absorption spectroscopy is a comparative technique, that is the determination of the concentration of a given element in a sample is carried out by comparing the absorption produced by the sample with that produced by a standard. In practice the absorption of a number of standards of differing concentrations, typically between 4 and 6 inclusive, is measured and a graph of absorption against concentration is obtained. The absorption of the sample is then measured and the concentration determined by means of the graph. In the context of atomic absorption spectroscopy the present invention is concerned with the validation of the calibration line and the determination of the reasons causing a non-valid calibration line. The method in its various aspects can diagnose the calibration line as one of the following:

1) A straight line of suitable quality for use in analysis of samples.

2) A straight line without sufficient precision to be used in analysis of samples.

3) A straight line with a blank problem, that is the absorbance of a standard of zero concentration is not zero.

4) The calibration line is curved.

5) The calibration line is curved at one end but has a linear portion.

6) The calibration line is straight but has one or more outliers.

Once the diagnosis into one of types 1) to 6) has been made, the analyst can then decide on the next appropriate steps to take. Thus in the first case the analyst will proceed to measuring the unknown samples confident that the calibration curve can be relied on. In the second case the analyst may repeat the measurement of the standards and if that does not produce a satisfactory line will then investigate whether the standards have been properly prepared or have become contaminated or whether different instrumental parameters might give better precision. In the third case again a remeasurement of the standards may be undertaken together with investigation of the blank solution and instrumental parameters. In the fourth case the analyst may again remeasure and/or change instrumental parameters in an attempt to obtain a straight line calibration curve or may accept a curved line and use a polynomial curve fitting routine. In the fifth case the analyst may restrict the measurement of samples to the linear portion of the calibration curve, that is only accept as a valid measurement samples of a concentration which lie on the straight line portion. In the sixth case, provided that sufficient good points remain, the analyst may use a calibration line which ignores the outlier point(s).

In atomic absorption spectroscopy it is often convenient to use aqueous standards but the samples may be in other matrices. For example, when measuring say lead in blood or in urine, these other matrices may interfere with the measured results giving erroneous values if a comparison with aqueous standards is used. In order to overcome this, the use of the technique of standards addition is known. This involves the construction of a further calibration line based on the measurement of the absorption of the sample to which has been added a given volume of a standard of known concentration. A plurality of these measurements are made with standards having different concentrations and a calibration line known as the standards addition line is produced. This is tested in a similar way to the normal calibration line. When good calibration and standards addition lines are obtained, their slopes are compared and if they are equal (within a given tolerance) it is concluded that no interference effects are present and consequently the aqueous standards calibration line can be used. If the slopes are not equal various known techniques can be adopted to reduce the matrix interferences.

Figure 2:
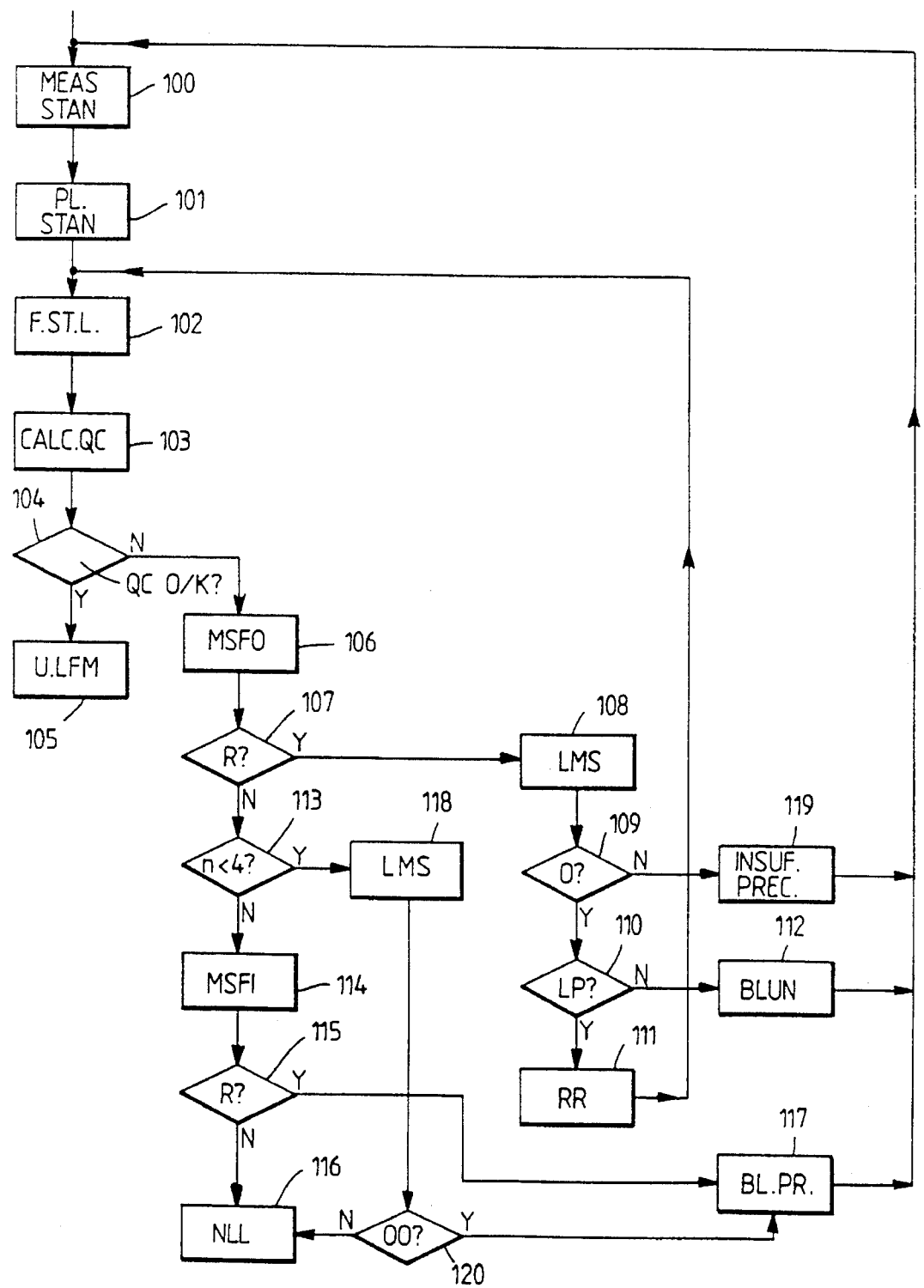
FIG. 2 is a flow diagram illustrating a method according to the invention of calibrating an atomic absorption spectrophotometer.

FIG. 2 is a flow diagram illustrating the method according to the invention when applied to atomic absorption spectroscopy. The first step of the method MEAS.STAN (Box 100) is to measure the absorbance of each of a plurality of standards of different known concentrations. The second step PL.STAN (Box 101) is to plot the measured absorbance against concentration. Of course, when using a computer for analysing the results this step may be purely conceptual in that a hard copy graph may not exist but merely be represented by data within the computer memory. The next step F.ST.L (Box 102) is to fit a straight line through the measured points and the origin using appropriate statistical techniques, for example the least squares method. A quality co-efficient is then calculated CALC.QC (Box 103). The quality co-efficient may for example be based on the co-efficient of quality proposed by Knecht and Stork. In this embodiment the quality co-efficient (QC) is defined as $$QC = 100 \times \left[ \frac{\sum_{i}^{N} \left( \frac{y_i - \hat{y}_i}{y_i} \right)^2}{N - 1} \right]^{1/2}$$

where $y_i$ is the measurement at each data point, $\hat{y}_i$ is the value predicted by the least squares line and N is the number of points, not including the zero point. A test is then made Q.C O/K? (Box 104) to determine whether the calculated quality co-efficient is within a given limit, for example 5%. If the answer is YES then an indication is given that the calibration line is satisfactory and may be used for performing sample measurements U.LFM (Box 105). This may be done via the video display unit of the computer either in the form of a good/bad display, by displaying the actual quality co-efficient, by displaying the calculated calibration curve, or by a combination of these. Alternatively, in a more fully automated system a proceed lamp may be illuminated on the spectrophotometer.

If the quality co-efficient is not within the given limit a number of further steps can be taken. The slopes of each of the measured points from the origin are determined MSFO (Box 106) and tested to see whether they are random or ordered R? (Box 107). As can be seen from FIG. 3, if the measured points are randomly scattered about the straight line it can be assumed that the problem is one of measurement precision. If this is so, then a line may be fitted using the least median of squares technique LMS (Box 108) and a test is then made to discover whether an outlier exists 0? (Box 109). If no outliers exist then the problem is one of general measurement precision and this can be indicated to the analyst INSUF.PREC (Box 119) who may then decide to relax the quality co-efficient required or may remeasure the standards in an attempt to improve the precision. If an outlier is found, a test is made to determine whether it is the last point on the line LP? (Box 110). If the answer is YES then a curvature of the calibration line at high concentrations is diagnosed and indicated RR (Box 111) and the analyst is advised to restrict the measurement range to the linear portion of the calibration line. If the answer is NO, that is the outlier is at an intermediate point, it is indicated that a false measurement has been made BLUN (Box 112). The analyst can then re-measure the appropriate standard or ignore the outlier. If curvature of the line at high concentrations is detected then the procedure from box 102 may be repeated with the last point deleted. This procedure may be repeated a number of times provided that a sufficient number of calibration points remain.

Figure 4:
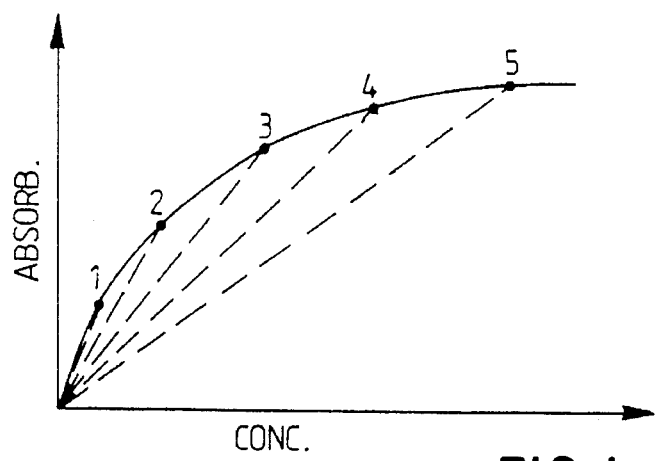
Figure 5:
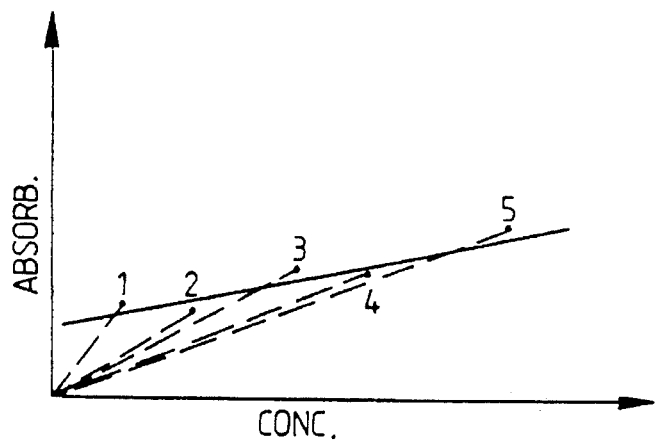
Figure 6:
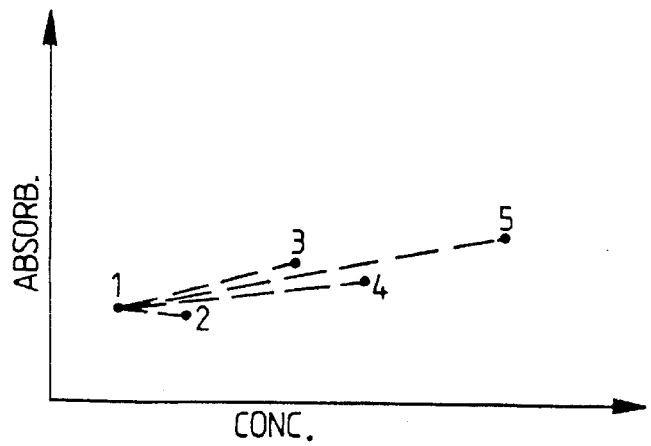

If in the test represented by Box 107 the answer is NO, that is the slopes are not random, this indicates that the calibration line is either curved as illustrated in FIG. 4 or is straight but does not pass through the origin as illustrated in FIG. 5. To determine which of these states is occurring, a test is made to see whether there are four or more standards n<4? (Box 113) and if so the slopes of the measured points are determined with respect to the first point rather than with respect to the origin MSFI (Box 114). A test is then carried out to determine whether these slopes are random R? (Box 115). If the answer is YES a blank problem is indicated BL.PR (Box 117) and the analyst will then normally investigate the reason for the blank problem, for example a contaminated blank solution, and then correct and re-measure the standards. If the answer is NO then the calibration line is curved and an indication is given to the analyst that the calibration line is non-linear NLL (Box 116).

It should be noted that if a decision at the 5% significance level is to be taken the tests 107 and 115 cannot be used with fewer than four standards since the probability of the occurrence of each permutation is too high. Consequently; with four standards only test 107 can be used since for test 115 only three slopes are left.

If the result of the test n<4? is YES then the calibration line is fitted using a robust regression method, such as the least medium of squares, LMS (Box 118) and a test is then made to determine whether the zero concentration absorbance is an outlier 0O? (Box 120). If it is then a blank problem is indicated BL.PR (Box 117) and if it is not then a non-linear calibration line is indicated NLL (Box 116).

Figure 3:
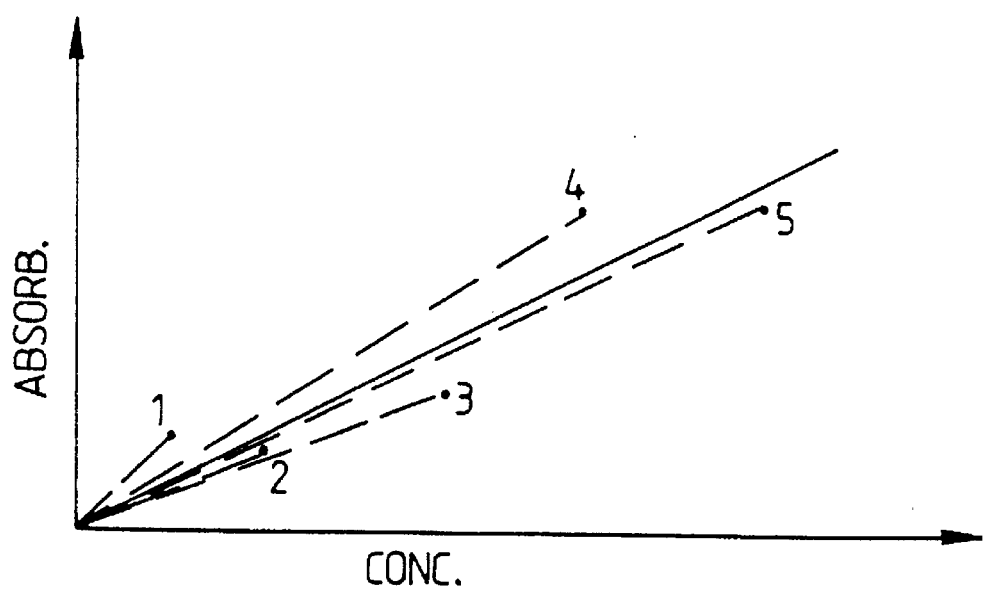
FIGS. 3, 4, 5, and 6 are illustrative calibration curves.

The tests 107 and 115 are based on the probability that if the calibration line is linear the measured points will be randomly distributed around the regression line as illustrated in FIG. 3. This has the consequence that the slope of the line joining the measurement points to the origin will be ranked randomly. That is in FIG. 3 slope 1>slope 4>slope 5>slope 2>slope 3. However, when there is systematic curvature as in FIG. 4 there will be ordered ranking. That is slope 1>slope 2>slope 3>slope 4>slope 5. There are n! different permutations possible where n is the number of measurement points. In other words, the slopes can be ranked in n! different ways. Consequently, each of these rankings has a probability of 1/n! . The specific ranking shown in FIG. 4 therefore has an occurrence probability of 1/120 or 0.8%. If such a ranking is found, it can be concluded that the line is not straight with a probability of rejecting straightness incorrectly of 0.8%.

This is subject to the condition illustrated in FIG. 5 which will be discussed later.

However, it is possible that for a non-linear calibration curve a strict ranking may not be obtained due to scatter of measurement points around the curve. Therefore, permutations where the ranking of two successive slopes is inverted may also be taken into account. For five data points four such inversions are possible, namely:

2>1>3>4>5
1>3>2>4>5
1>2>4>3>5
1>2>3>5>4

If these permutations are taken into account, the probability of rejecting straightness is still smaller than 5%

For calibration lines with four standards, no inversions can be allowed since the probability of systematic ranking is already 4%.

For calibration lines with six standards, permutations containing up to three inversions of successive slopes, for example 2>1>4>3>6>5, may be allowed while maintaining a probability of rejecting a straight line incorrectly of less than 5%.

Clearly, as the number of standards is increased so the number of given orders can be increased while still having a small probability of incorrectly rejecting a straight line.

The test 115 is used to distinguish between a curved calibration line and a straight line which does not pass through the origin and hence is either a standards addition line or is a calibration line where a blank problem exists. As can be seen, if the curve shown in FIG. 5 is considered the slopes of standards 1 to 5 are ordered. That is slope 1>slope 2>slope 3>slope 4>slope 5. However, if the slopes are now measured with respect to standard 1, then they become random. That is slope 3>slope 5>slope 4>slope 2. In order for this test to be valid at least four standards need to be measured. If less than four standards are measured, the probability of incorrectly rejecting a straight line becomes high and test 115 is less useful.

Figure 7:
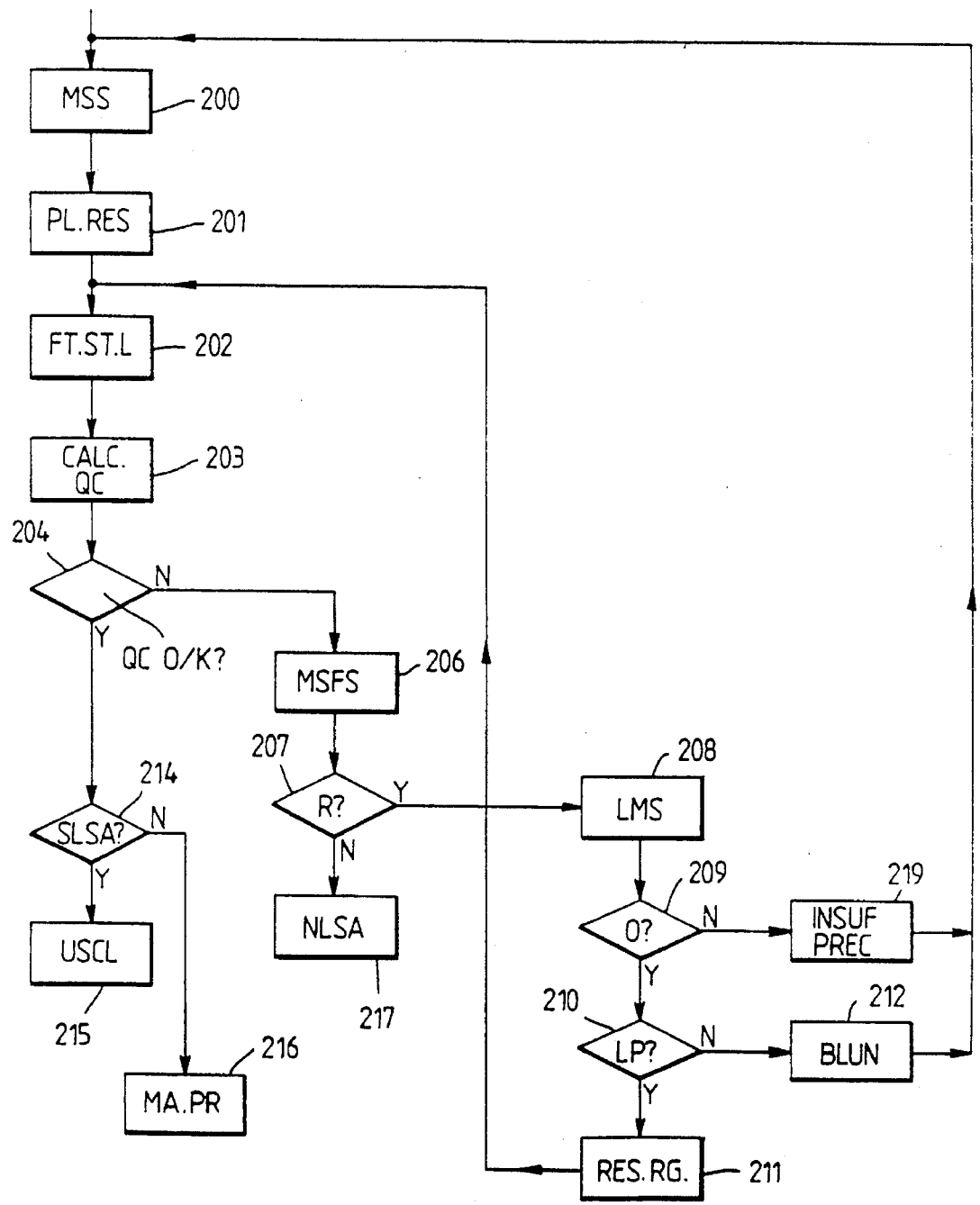
FIG. 7 is a flow diagram illustrating a method according to the invention of calibrating an atomic absorption spectrophotometer using the standards addition technique.

A similar procedure is followed for a standards addition line and is illustrated in FIG. 7. The first step is to measure the absorbance of a sample and the absorbance of a plurality of standards added to the sample MSS (Box 200). The measured results are then plotted PL.RES (Box 201) and a straight line fitted to the plotted points using an appropriate statistical technique FT.ST.L (Box 202). A quality co-efficient is then calculated CALC.QC (Box 203) and then tested to determine whether it falls within a given limit QC O/K? (Box 204). If it does then the slope of the standards addition line is compared with that of the aqueous standards calibration line SLSA? (Box 214) and if they are the same (within predetermined limits) then an indication is given that the aqueous standards calibration line can be used for the measurement of samples USCL (Box 215). If the slopes are unequal then it is indicated that a matrix problem exists MA.PR (Box 216) and the analyst would then take appropriate action to minimise the matrix interferences.

If the quality co-efficient of the line is not acceptable, that is the answer to the test QC O/K? (Box 204) is NO then a similar procedure to that described with reference to FIG. 2 is carried out. There are some differences, however, which will become apparent from the following description. The slopes of the plotted points are determined with reference to the sample measurement point MSFS (Box 206) rather than with respect to the origin since there will always be a sample absorbance. It is then determined whether these slopes are random or ordered R? (Box 207). If they are ordered then a non-linear standards addition line is indicated NLSA (Box 217). It will be appreciated that this corresponds to the test 115 in FIG. 2 as the test 107 is not applicable to the standards addition line as it does not pass through the origin, that is there is always an absorbance at the zero standard concentration due to the presence of the sample.

If the slopes are random then a robust regression technique such as the least median of squares is used to fit the line to the points LMS (Box 208). A test is then made to see if there are any outliers 0? (Box 209). If the answer is NO then insufficient precision of measurement is indicated, INSUF.PREC (Box 219), to the analyst who may then decide to relax the quality co-efficient required or may perform the standards addition analysis again in an attempt to improve the precision. If the answer is YES then a further test is made to determine whether the last point is an outlier LP? (Box 210) and if the answer is YES then an indication that the measurement range should be restricted RES.RG (Box 211) is made and the procedure from Box 202 is repeated with the last point omitted. If the last point is an outlier it is reasonable to assume that curvature of the line is occurring at high absorbances. If the outlier is not the last point then a measurement error is indicated BLUN (Box 212) and the analyst will then re-measure at least the point which is an outlier.

While the method has been described as applied to atomic absorption spectroscopy it will be apparent that it is applicable to the generation and testing of calibration lines for any comparative measurement technique.

For example the method is also applicable to X-ray analysis such as X-ray spectrometry and X-ray diffraction measurement, particularly for quantitive phase analysis. In this case in FIG. 1 reference 1 represents an X-ray spectrometer such as that sold by Philips Analytical under the type reference PW 1480 rather than an atomic absorption spectrometer. X-ray spectrometry is, like atomic absorption spectrometry, a comparative technique and the intensity of X-rays received by the detector is an indication of the concentration of the sample. However in order to determine the concentration of a selected substance in a sample the use of a calibration curve is required. Thus the intensity of the X-rays received by the detector for a series of standards of varying concentrations is measured and plotted to produce a graph of intensity against concentration in similar fashion to the atomic absorption calibration curve of absorption against concentration. The concentration of a given sample can then be determined by measuring the received X-ray intensity and reading off the calibration curve the corresponding concentration. Clearly the same conditions apply when producing the calibration curve for X-ray spectrometry as when producing that for atomic absorption spectroscopy though the steps taken to correct for unsatisfactory calibration curves may differ in view of the different analytical techniques and physical principles on which they are founded.

From reading the present disclosure, other modifications will be apparent to persons skilled in the art. Such modifications may involve other features which are already known in the design and use of analytical instruments and component parts thereof and which may be used instead of or in addition to features already described herein. Although claims have been formulated in this application to particular combinations of features, it should be understood that the scope of the disclosure of the present application also includes any novel feature or any novel combination of features disclosed herein either explicitly or implicitly or any generalisation of one or more of those features which would be obvious to persons skilled in the art, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

I claim:

1. A method of calibrating an X-ray spectrometer comprising the steps of
   (a) generating x-rays from at least one standard sample,
   (b) measuring intensities of said x-rays for different concentrations of said standard sample,
   (c) forming a representation of intensity versus concentration for each measured value of intensity with said different concentrations,
   (d) determining if a best straight calibration line can be formed from said representation, and if not
   (e) changing instrument parameters and/or sample preparation to achieve said best straight calibration line, and
   (f) repeating said steps (a)–(d) to calibrate said x-ray spectrometer.

2. A method of calibrating according to claim 1, wherein at least four of said standard samples with different concentrations are used.

3. A method according to claim 2, wherein at most six of said standard samples with different concentrations are used.

4. A method according to claim 1, wherein at most six of said standard samples with different concentrations are used.

5. A method of calibrating an atomic absorption spectrophotometer comprising the steps of
   (a) generating electrical signals from at least one standard sample,
   (b) converting said electrical signals into absorbance values of said standard sample for different concentrations of said standard sample,
   (c) forming a representation of absorbance versus concentration for each absorbance value with said different concentrations,
   (d) determining if a best straight calibration line can be formed from said representation, and if not,
   (e) changing instrument parameters and/or sample preparation to achieve said best straight calibration line, and
   (f) repeating said steps (a)–(d) to calibrate said atomic absorption spectrometer.

6. A method of calibrating according to claim 5, wherein at least four of said standard samples with different concentrations are used.

7. A method according to claim 6, wherein at most six of six standard samples with different concentrations are used.

8. A method according to claim 6, wherein at most six of six standard samples with different concentrations are used.

* * * * *